United States Patent [19]

Hoel

[11] Patent Number: 5,569,271
[45] Date of Patent: Oct. 29, 1996

[54] SURGICAL INSTRUMENT FOR SUTURING

[76] Inventor: Steven B. Hoel, 701 Orchard, Longview, Tex. 75601

[21] Appl. No.: 534,023

[22] Filed: Sep. 26, 1995

Related U.S. Application Data

[63] Continuation of Ser. No. 131,443, Oct. 4, 1993, abandoned.
[51] Int. Cl.$^6$ .......................... A61B 17/04; A61B 17/28
[52] U.S. Cl. ................................. 606/148; 606/207
[58] Field of Search .................................. 606/144, 145, 606/146, 147, 148, 207, 205, 151

[56] References Cited

U.S. PATENT DOCUMENTS

| | | |
|---|---|---|
| 292,643 | 1/1884 | Friend . |
| 486,486 | 11/1892 | Lewis . |
| 1,653,803 | 12/1927 | Fisher . |
| 2,743,726 | 5/1956 | Grieshaber ........................... 128/321 |
| 4,553,543 | 11/1985 | Amarasinghe ....................... 128/334 |
| 4,957,498 | 9/1990 | Caspari et al. ....................... 606/146 |
| 5,002,561 | 3/1991 | Fisher ................................... 606/205 |
| 5,143,414 | 1/1992 | Rosellini ............................. 294/99.2 |
| 5,254,126 | 10/1993 | Filipi et al. ......................... 606/146 |

*Primary Examiner*—Michael Powell Buiz
*Assistant Examiner*—Nancy Mulcare
*Attorney, Agent, or Firm*—Crutsinger & Booth

[57] ABSTRACT

A surgical device is used for manually manipulating suture needles. The device is formed of two elongate members hinged together. On one side of the hinge, the elongate members form a pair of jaws which are relatively moveable. One the other end of the elongate members there are handles formed which allow the user to manipulate the jaws about the hinge. An arcuate shield is integral with one of the jaws at its center. The shield extends laterally and arcuately from the jaw and covers the opposing jaw. The placement of the shield is such that a needle which is held between the jaws is protected from sticking any one or anything. The jaw members may be made up of several units forming segmented jaws.

5 Claims, 1 Drawing Sheet

U.S. Patent    Oct. 29, 1996    5,569,271
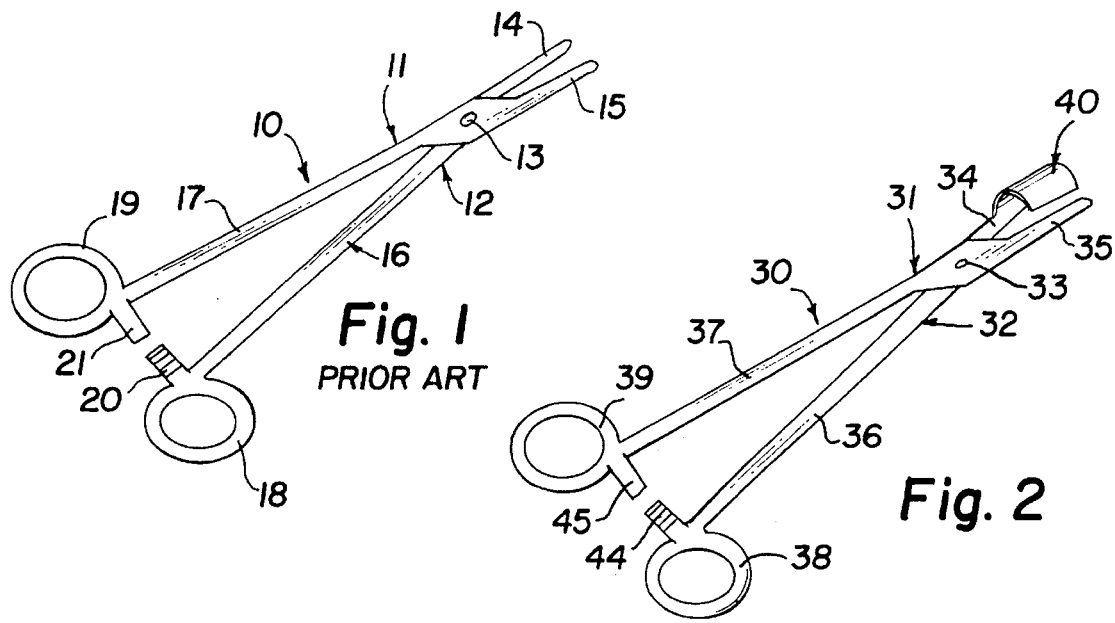
Fig. 1
PRIOR ART
Fig. 2
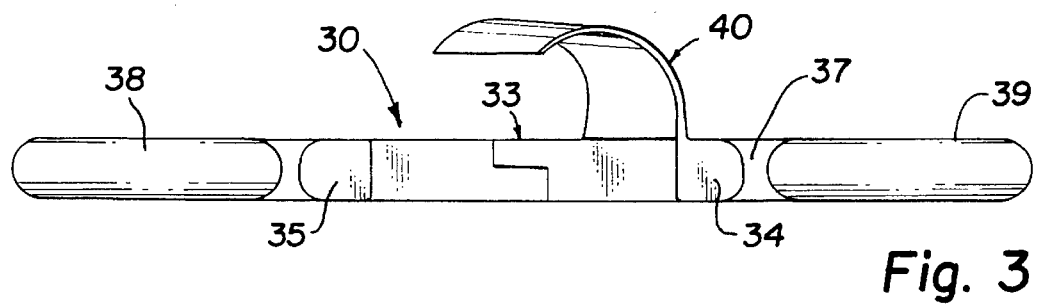
Fig. 3
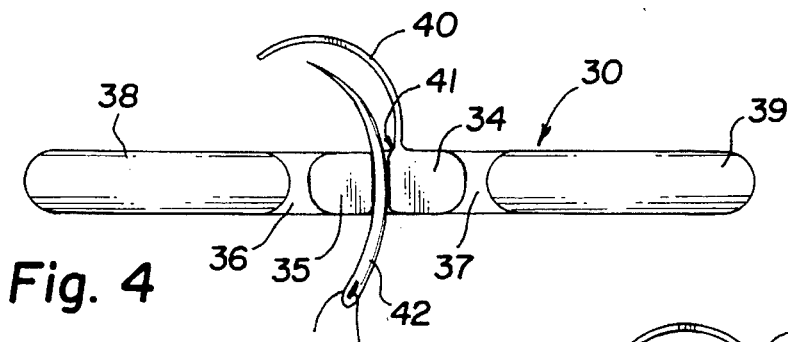
Fig. 4
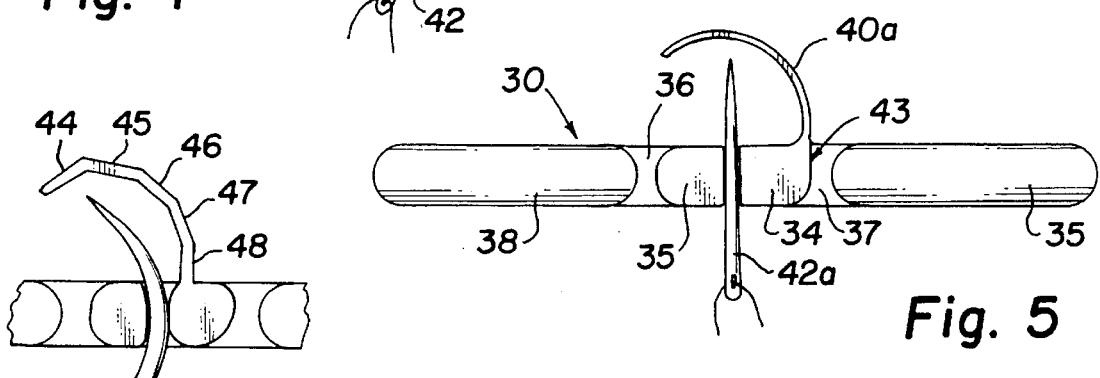
Fig. 5
Fig. 6

SURGICAL INSTRUMENT FOR SUTURING

This is a continuation of application Ser. No. 08/131,443, filed Oct. 4, 1993, now abandoned.

BACKGROUND OF INVENTION

This invention relates to surgical instruments, more particularly to a surgical instrument for use in surgical suturing.

In certain surgical procedures the physician or surgeon must suture two sides of tissue together. This is accomplished by passing the point of a needle, often a curved needle, through the two sides of tissue successively or simultaneously and then pulling the remainder of the needle body through the tissue to carry the suture thread with it. The needle may be pulled or driven completely through by hand or using instruments such as needle drivers, hemostats or similar plier-like devices. Whether the needle is cleared by hand or by instruments there will be an exposed needle point being moved around a confined space, usually with numerous nurses' or surgeons' hands, fingers, wrists or other parts in close proximity. There is obviously considerable opportunity for accidental needle-prick of those hands, fingers or wrists, a prick that in recent years is potentially lethal to those receiving the wound no matter how minor.

It is an object of the present invention to provide a surgical instrument adapted for driving, manipulating and extracting or clearing a suture needle with means protecting against accidental pricks by the needle point of persons who must have their fingers or hands near the suturing site during surgical procedures.

SUMMARY OF INVENTION

The present invention provides a needle-driving instrument having an integral shield to prevent accidental needle pricks of personal conducting or assisting in surgical procedures.

According to the principles of the invention, there is provided a plier-like instrument with a pair of elongated members pivotally hinged to each other at a point between their midpoints and one of their ends to provide relatively long handles and relatively short "jaws" or clamp ends. The "jaw" or clamp end of one of the members is provided with a curved shield plate positioned to guard the point of the needle held properly between the jaw members.

BRIEF DESCRIPTION OF THE DRAWINGS

The present invention can be more readily understood from the following detailed description when read in conjunction with the accompanying drawings wherein:

FIG. 1 is a perspective view of a typical needle-driver of the prior art;

FIG. 2 is a perspective view of a the needle-driver/retriever of the present invention showing the needle-shield element;

FIG. 3 is a front elevation view of the needle driver/retriever of the present invention in the open position;

FIG. 4 is a front elevation view of the needle driver/retriever of the present invention illustrating the manner in which a curved suture needle is gripped by the needle and used;

FIG. 5 is an front elevation view of the needle driver/retriever of the present invention of a slightly modified form to better accommodate the gripping and shielding of a straight suture needle as shown; and FIG. 6 is a front elevation view, partially cut away, of the needle driver/retriever of the present invention having a slightly modified field structure.

DETAILED DESCRIPTION OF THE INVENTION

When referring to the drawings hereinafter, like elements and features of the invention are designated by the same reference numbers or same identifications throughout the various figures.

With reference now to FIG. 1 there is shown in a perspective view a typical form of a metal surgical clamp designated generally as 10 of a type often used in the prior art as a needle-driver/retriever in surgical procedures. The clamp 10 is comprised of a pair of elongated members, 11 and 12, pivotally hinged at 13 to form jaw elements or sections 14 and 15, handle elements or sections 16 and 17 with grip loops 18 and 19 for better controlled manipulation. Also provided near the loops are small ratchet tabs, 20 and 21, forming a releasable pressure sustaining lock mechanism for holding the jaws clamped on an object between them.

The needle driver/retriever of the present invention, in its preferred embodiment, is shown in FIGS. 2–5 and is similar in its handle area to the prior art clamp of FIG. 1 thus providing a certain familiarity of "feel" and operation to the user.

As shown, the needle driver/retriever of the present invention designated generally as 30 comprises a pair of relatively thin, elongated members 31 and 32 pivotally hinged together preferably closer to one end than to the other. The shorter portions of the two pivoted members form a pair of "jaws," 34 and 35. The jaws may be shaped with generally flattened inwardly facing (opposing) surfaces to provided clamping action. The larger ends of the pivoted members form handle members, 36 and 37, and in the preferred embodiment terminate in grip loops, 38 and 39. As in the prior art, the needle driver/retriever is provided with ratchet tabs, 40 and 41, as releasable clamp hold mechanisms. Thus the handle ends of the needle driver/retriever of the present invention will have a familiar "feel" to users who are experienced with FIG. 1 type prior art clamps.

Added to and integral with one of the jaw elements, 34, of the driver/retriever 30, is a shield element, 40, which in the preferred embodiment is in the form of a small curved plate that extends longitudinally for most of the length of the jaw portion, 34. The shield element 40 extends laterally from the jaw element on which it is mounted or of which it s a part curving over the opposite jaw as shown so that anything held between the driver jaws is protected from accidental or unintentional contact with other objects.

The driver 30 may be made of plastic or metal material such as that used in prior art clamps but preferably is of a stainless steel to provide desirable overall strength, a springy resiliency in the handles and a high resistance to breakage. The member 31 and 32 may be of generally round, oval or rectangular (with rounded edge) cross-section over most of their length with an appropriate shape about the pivot point to form the hinge as is well known in the art. The shield 40 is to be of an appropriate thickness to be relatively stiff and resistant to bending.

As may be seen in the end view of FIG. 4, the shield 40 may be made as an extension of the inner-clamp face 41 of jaw element 34 and be formed in a sufficiently wide arc to clear, yet shield, a curved suture needle, 42, clamped between the jaws 34 and 35 as it would be at times during use.

When used in conjunction with a straight suture needle such as needle 42a in FIG. 5 it may be preferable to construct the shield 40a as an extension of the outer-face or surface 43 of jaw 37a as shown. In such a construction, the straight needle may be held between the clamped jaws at a greater distance from its point without the needle point touching the shield than would be the case in the construction of FIG. 4.

Obviously the shield extending from the outer-face of the clamp jaw 37a of FIG. 5 maybe shaped to accommodate either a curved or straight needle. Thus, the present invention contemplates use of shield forms not of the smooth-even curves shown in the embodiment illustrated in FIGS. 3, 4 and 5 of the drawings. For example, the shield may be straight or flat along a portion of its lateral-extent or it may comprise two or more flat, planer sections 44, 45, 46, 47 and 48 connected together to form an angled shielding structure as shown in FIG. 6.

Thus, there have been disclosed specific embodiments of the shield needle driver/retriever of the present invention. It is understood that this invention is to be in no way limited to the illustrated structures but is to be construed to include in and all variations and modifications that may occur to those skilled in the art, still within the spirit of the invention and is to be limited only as set forth in the following claims when read in their true scope.

What is claimed is:

1. In a clamp device of the type used for driving, manipulating, clearing and extracting a suture needle in surgical procedures that comprises a pair of elongated members pivotally hinged to each other at a point along their lengths between their midpoints and their first ends to form a pair of jaw sections extending from about said hinge point to said first end and to form a pair of handle sections from about the hinge point to the second ends of said members, said jaw sections being adapted to clamp and hold therebetween a suture needle near its midsection with the ends of said needle extending laterally from between said jaw sections, the improvement comprising: a shield plate affixed to one of said jaw sections over essentially the full length of said one jaw section and extending laterally outward and arcuately over the other of said jaw sections so as to shield from accidental contact with other objects one end of a suture needle clamped between said jaw sections near the midsection of said suture needle for manipulation of said needle by a user of said clamp device.

2. The clamp device improvement as defined in claim 1 wherein said shield plate is an integral part of said one jaw section.

3. The clamp device improvement as defined in claim 1 wherein said shield plate comprises a plurality of flat planer sections joined at their longitudinal edges.

4. The clamp device improvement as defined in claim 2 wherein the inner surface of said shield member extends from the inner surface of said one jaw section that faces said other jaw section.

5. The clamp device improvement as defined in claim 2 wherein the outer surface of said shield plate extends from the outer surface of said one jaw section that faces away from said other jaw section.

\* \* \* \* \*